(12) United States Patent
Zucherman et al.

(10) Patent No.: US 7,189,234 B2
(45) Date of Patent: Mar. 13, 2007

(54) INTERSPINOUS PROCESS IMPLANT SIZER AND DISTRACTOR WITH A SPLIT HEAD AND SIZE INDICATOR AND METHOD

(75) Inventors: James F Zucherman, San Francisco, CA (US); Ken Y Hsu, San Francisco, CA (US); Charles A Hartjen, Monkton, MD (US); Charles J Winslow, Walnut Creek, CA (US); John Flynn, Concord, CA (US); David Bohrer, Barrington, RI (US)

(73) Assignee: St. Francis Medical Technologies, Inc., Alameda, CA (US)

( * ) Notice: Subject to any disclaimer, the term of this patent is extended or adjusted under 35 U.S.C. 154(b) by 0 days.

(21) Appl. No.: 09/999,754

(22) Filed: Oct. 31, 2001

(65) Prior Publication Data

US 2002/0072752 A1   Jun. 13, 2002

Related U.S. Application Data

(63) Continuation-in-part of application No. 09/799,470, filed on Mar. 5, 2001, now Pat. No. 6,902,566, which is a continuation-in-part of application No. 09/799,215, filed on Mar. 5, 2001, now Pat. No. 7,101,375, which is a continuation-in-part of application No. 09/473,173, filed on Dec. 28, 1999, now Pat. No. 6,235,030, which is a continuation-in-part of application No. 09/474,037, filed on Dec. 28, 1999, now Pat. No. 6,190,387, which is a continuation of application No. 09/179,570, filed on Oct. 27, 1998, now Pat. No. 6,048,342, which is a continuation-in-part of application No. 09/175,645, filed on Oct. 20, 1998, now Pat. No. 6,068,630.

(60) Provisional application No. 60/323,508, filed on Sep. 18, 2001.

(51) Int. Cl.
 *A61B 17/56* (2006.01)
(52) U.S. Cl. .................. 606/61; 606/205; 600/219; 600/235
(58) Field of Classification Search ............ 606/60, 606/61, 63, 64, 90, 205; 600/201, 210, 219, 600/225, 235
See application file for complete search history.

(56) References Cited

U.S. PATENT DOCUMENTS

| | | | |
|---|---|---|---|
| 2,456,806 A | * | 12/1948 | Wolffe |
| 2,677,369 A | | 5/1954 | Knowles |
| 3,426,364 A | | 2/1969 | Lumb |
| 3,648,691 A | | 3/1972 | Lumb et al. |
| 3,867,728 A | | 2/1975 | Stubstad et al. |
| 3,875,595 A | | 4/1975 | Froning |
| 4,309,777 A | | 1/1982 | Patil |
| 4,349,921 A | | 9/1982 | Kuntz |
| 4,369,769 A | | 1/1983 | Edwards |
| 4,401,112 A | | 8/1983 | Rezaian |
| 4,479,491 A | | 10/1984 | Martin |
| 4,501,269 A | | 2/1985 | Bagby |
| 4,553,273 A | | 11/1985 | Wu |
| 4,554,914 A | | 11/1985 | Kapp et al. |
| 4,599,084 A | | 7/1986 | Nashef |
| 4,599,086 A | | 7/1986 | Doty |
| 4,604,995 A | | 8/1986 | Stephens et al. |
| 4,611,582 A | | 9/1986 | Duff |
| 4,636,217 A | | 1/1987 | Ogilvie et al. |
| 4,643,178 A | | 2/1987 | Nastari et al. |
| 4,657,550 A | | 4/1987 | Daher |
| 4,685,447 A | | 8/1987 | Iversen et al. |
| 4,696,290 A | | 9/1987 | Steffee |
| 4,714,469 A | | 12/1987 | Kenna |
| 4,743,256 A | | 5/1988 | Brantigan |
| 4,772,287 A | | 9/1988 | Ray et al. |
| 4,790,303 A | | 12/1988 | Steffee |
| 4,834,757 A | | 5/1989 | Brantigan |
| 4,878,915 A | | 11/1989 | Brantigan |
| 4,904,260 A | | 2/1990 | Ray et al. |
| 4,904,261 A | | 2/1990 | Dove et al. |
| 4,913,134 A | | 4/1990 | Luque |
| 4,932,975 A | | 6/1990 | Main et al. |
| 4,936,848 A | | 6/1990 | Bagby |
| 4,946,378 A | | 8/1990 | Hirayama et al. |

| | | | | | | |
|---|---|---|---|---|---|---|
| 4,961,740 A | 10/1990 | Ray et al. | | 6,565,570 B2 * | 5/2003 | Sterett et al. ............. 606/69 |
| 4,969,888 A | 11/1990 | Scholten et al. | | 6,582,437 B2 | 6/2003 | Dorchak ................. 606/90 |
| 5,011,484 A | 4/1991 | Breard | | 6,755,841 B2 | 6/2004 | Fraser .................... 606/99 |
| 5,015,247 A | 5/1991 | Michelson | | 6,770,095 B2 | 8/2004 | Grinberg |
| 5,026,373 A | 6/1991 | Ray et al. | | 2001/0012938 A1 | 8/2001 | Zucherman |
| 5,035,716 A | 7/1991 | Downey | | 2004/0106998 A1 | 6/2004 | Ferree |
| 5,047,055 A | 9/1991 | Bao et al. | | 2004/0138750 A1 | 7/2004 | Mitchell |
| 5,055,104 A | 10/1991 | Ray | | 2004/0143332 A1 | 7/2004 | Krueger |
| 5,059,193 A | 10/1991 | Kuslich | | | | |
| 5,059,194 A | 10/1991 | Michelson | | | | |
| 5,084,049 A | 1/1992 | Asher et al. | | | | |
| 5,092,866 A | 3/1992 | Breard et al. | | | | |

FOREIGN PATENT DOCUMENTS

| | | |
|---|---|---|
| CA | 2015507 | 1/1991 |
| DE | 2821678 A1 | 4/1980 |
| DE | 3113142 A1 | 1/1982 |
| EP | 140790 A2 | 10/1984 |
| EP | 146347 A1 | 12/1984 |
| EP | 322334 A1 | 12/1988 |
| EP | 0677277 A2 | 10/1995 |
| EP | 0767636 B1 | 4/1997 |
| EP | 1138268 | 4/2001 |
| FR | WO 90/00037 | 1/1990 |
| FR | 2681525 A1 | 3/1993 |
| FR | 2705227 | 11/1994 |
| FR | 2707864 A1 | 1/1995 |
| FR | 2717675 | 9/1995 |
| FR | 2722088 | 1/1996 |
| FR | 2722980 A1 | 2/1996 |
| FR | 2724554 | 3/1996 |
| FR | 2780269 A1 | 12/1999 |
| FR | 2782911 A1 | 3/2000 |
| FR | 2806614 | 9/2001 |
| FR | 2806616 | 9/2001 |
| GB | 780652 | 8/1957 |
| SU | 1484348 A1 | 6/1989 |
| WO | WO 91/16018 | 10/1991 |
| WO | WO 94/21185 | 9/1994 |
| WO | WO 94/26192 | 11/1994 |
| WO | WO 98/48717 | 11/1998 |
| WO | WO 99/26562 | 6/1999 |
| WO | WO 99/40866 | 8/1999 |
| WO | WO 99/42051 | 8/1999 |
| WO | WO 99/59669 | 11/1999 |
| WO | WO 00/04851 | 2/2000 |
| WO | WO 00/13619 | 3/2000 |
| WO | WO 00/13620 | 3/2000 |
| WO | WO 01/28442 A1 | 4/2001 |

| | | |
|---|---|---|
| 5,122,130 A * | 6/1992 | Keller .................. 606/61 |
| 5,123,926 A | 6/1992 | Pisharodi |
| 5,167,662 A | 12/1992 | Hayes et al. |
| 5,180,381 A | 1/1993 | Aust et al. |
| 5,192,327 A | 3/1993 | Brantigan |
| 5,258,031 A | 11/1993 | Salib et al. |
| 5,263,953 A | 11/1993 | Bagby |
| 5,290,312 A | 3/1994 | Kojimoto et al. |
| 5,304,178 A | 4/1994 | Stahurski |
| 5,306,309 A | 4/1994 | Wagner et al. |
| 5,352,225 A | 10/1994 | Yuan et al. |
| 5,387,213 A | 2/1995 | Breard et al. |
| 5,390,683 A | 2/1995 | Pisharodi |
| 5,395,372 A | 3/1995 | Holt et al. |
| 5,415,661 A | 5/1995 | Holmes |
| 5,443,514 A | 8/1995 | Steffee |
| 5,454,812 A | 10/1995 | Lin |
| 5,458,638 A | 10/1995 | Kuslich et al. |
| 5,458,641 A | 10/1995 | Ramirez Jimenez |
| 5,458,643 A | 10/1995 | Oka et al. |
| 5,470,333 A | 11/1995 | Ray |
| 5,496,318 A | 3/1996 | Howland et al. |
| 5,505,732 A | 4/1996 | Michelson |
| 5,514,180 A | 5/1996 | Heggeness et al. |
| 5,527,312 A | 6/1996 | Ray |
| 5,534,028 A | 7/1996 | Bao et al. |
| 5,534,029 A | 7/1996 | Shima |
| 5,540,689 A | 7/1996 | Sanders et al. |
| 5,549,679 A | 8/1996 | Kuslich |
| 5,554,191 A | 9/1996 | Lahille et al. |
| 5,562,736 A | 10/1996 | Ray et al. |
| 5,593,409 A | 1/1997 | Michelson |
| 5,609,634 A | 3/1997 | Voydeville |
| 5,645,597 A | 7/1997 | Krapiva |
| 5,645,599 A | 7/1997 | Samani |
| 5,653,761 A | 8/1997 | Pisharodi |
| 5,674,295 A | 10/1997 | Ray et al. |
| 5,674,296 A | 10/1997 | Bryan et al. |
| 5,676,702 A | 10/1997 | Ratron |
| 5,702,455 A | 12/1997 | Saggar |
| 5,725,582 A | 3/1998 | Bevan et al. |
| 5,766,252 A | 6/1998 | Henry et al. |
| 5,800,438 A * | 9/1998 | Tuke et al. .............. 606/90 |
| 5,824,098 A | 10/1998 | Stein |
| 5,865,846 A | 2/1999 | Bryan et al. |
| 5,885,299 A | 3/1999 | Winslow et al. |
| 5,888,224 A | 3/1999 | Beckers et al. |
| 5,888,226 A | 3/1999 | Rogozinski |
| 5,976,186 A | 11/1999 | Bao et al. |
| 6,001,130 A | 12/1999 | Bryan et al. |
| 6,022,376 A | 2/2000 | Assell et al. |
| 6,048,342 A | 4/2000 | Zucherman |
| 6,068,630 A | 5/2000 | Zucherman |
| 6,113,639 A | 9/2000 | Ray et al. |
| 6,156,067 A | 12/2000 | Bryan et al. |
| 6,190,414 B1 | 2/2001 | Young et al. |
| 6,234,705 B1 | 5/2001 | Troxel |
| 6,261,296 B1 * | 7/2001 | Aebi et al. ............. 606/90 |
| 6,368,351 B1 | 4/2002 | Glenn et al. |
| 6,425,901 B1 * | 7/2002 | Zhu et al. ............. 606/142 |
| 6,458,131 B1 | 10/2002 | Ray |

OTHER PUBLICATIONS

Minns, R.J., et al., *Preliminary Design and Experimental Studies of a Novel Soft Implant for Correcting Sagittal Plane Instability in the Lumbar Spine*, SPINE vol. 22, No. 16, pp. 1819-1825, © 1997, Lippincott-Raven Publishers.

Waldemar Link, brochure entitled *Wirbelsäulen-Chirurgie: Instrumentarium Und Implantate Zur Wirbelsäulen-Chirurgie* (SpinalSurgery: Instrumentation and Implants for Spinal Surgery), Waldermar Link, Hamburg, Germany.

Haruo Tsuji, et al., *Ceramic Interspinous Block (CISB) Assisted Anterior Interbody Fusion*, Journal of Spinal Disorders, vol. 3, No. 1, pp. 77-86, © 1990 Raven Press, Ltd., New York.

Richard W. Porter, MD, FRCS, FRCSE, *Spinal Stenosis and Neurogenic Claudication*, SPINE vol. 21, No. 17, pp. 2046-2052, © 1996, Lippincott-Raven Publishers.

"Patton Speculum™ Complete Cervical Visualization," Patton Medical Speculum Product Information, http://www.patton-medical.com/Speculum1.html, downloaded May 25, 2001, 1 page.

"Speculum and Lasik Instruments," WPI-Medical Speculum, Lasik Instruments, http://www.wpi-medical.com/Specu__Lasik_pgs/lasik.html, downloaded May 25, 2001, 1 page.

JPEG image 172×192 pixels, http://www.fraudoktor.com/medical/pix/cusco.jpg, downloaded May 25, 2001, 1 apge.

JPEG image 166×173 pixels, http://www.fraudoktor.com/medical/piz/trelat1.jpg, downloaded May 25, 2001, 1 page.

JPEG image 294×324 pixels, http://www.fraudoktor.com/medical/pix/guttmann.jpg, downloaded May 25, 2001, 1 page.

"Semm," JPEG image 173×311 pixels, http://www.fraudoktor.com/medical/pix/semm.jpg, downloaded May 25, 2001, 1 page.

"Seyffert," JPEG image 191×347 pixels, http://www.fraudoktor.com/medical/pix/seyffert.jpg, downloaded May 25, 2001, 1 page.

"O'Sullivan O'Connor," JPEG image 188×409 pixels, http://www.fraudoktor.com/medical/pix/osoc.jpg, downloaded May 25, 2001, 1 page.

JPEG image 152×166 pixels, http://www.fraudoktor.com/medical/pix/4bs6.jpg, downloaded May 25, 2001, 1 page.

Cousin Biotech, Brochure in French and English, *Dispositif Intervertebral Amortissant*, Jun. 1998.

\* cited by examiner

*Primary Examiner*—Ralph A. Lewis

(74) *Attorney, Agent, or Firm*—Fliesler Meyer LLP

(57) ABSTRACT

The present invention enables a physician to distract a previously created opening, determine the size of the opening, and alternatively, subsequently assist in inserting an implant between adjacent spinous processes. The distracting device has two prongs which separate as the handle of the device is closed. When the spinous processes are distracted to a desired diameter, the physician can lock the prongs in place, allowing him to determine and select an appropriately sized implant.

4 Claims, 8 Drawing Sheets

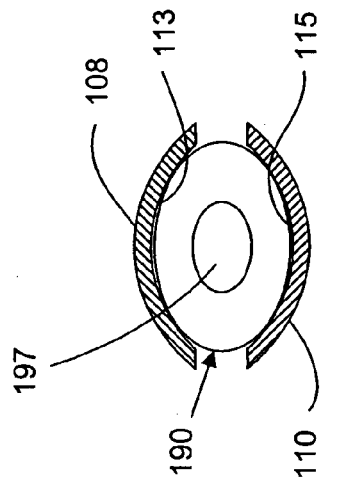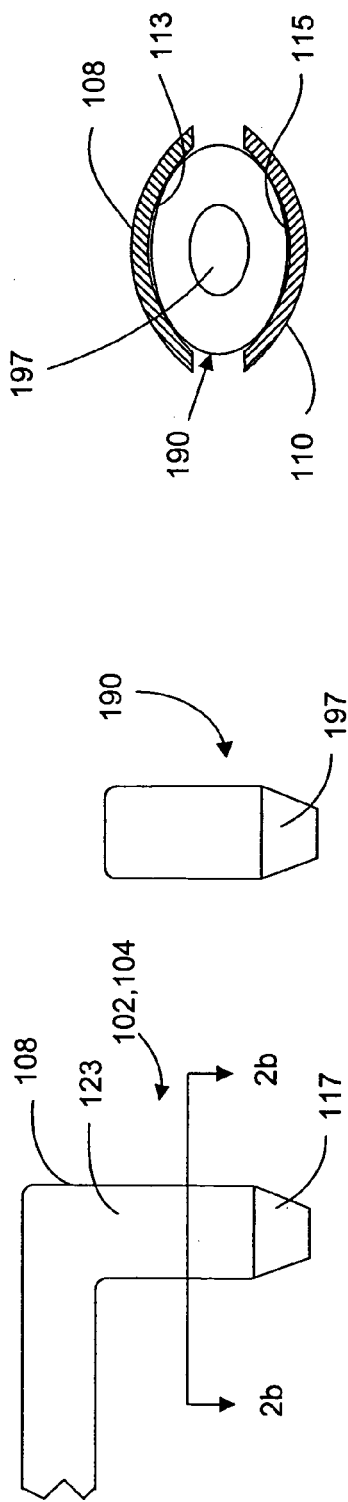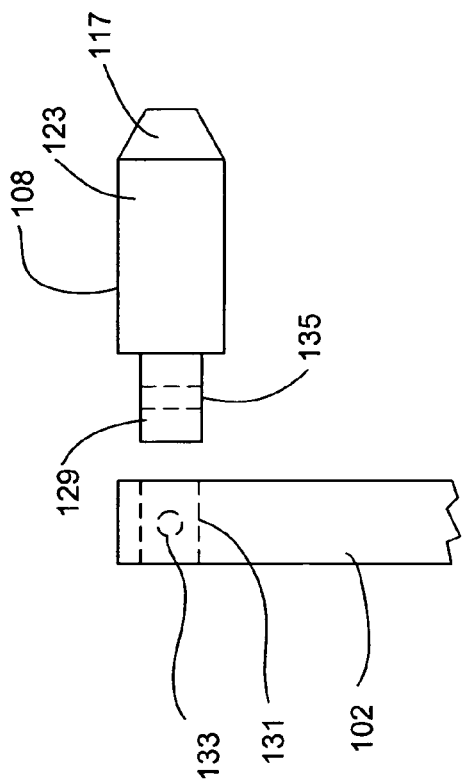

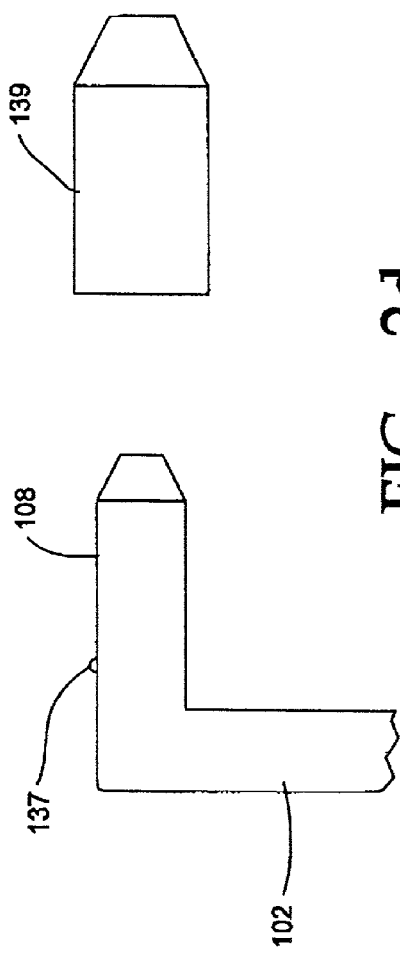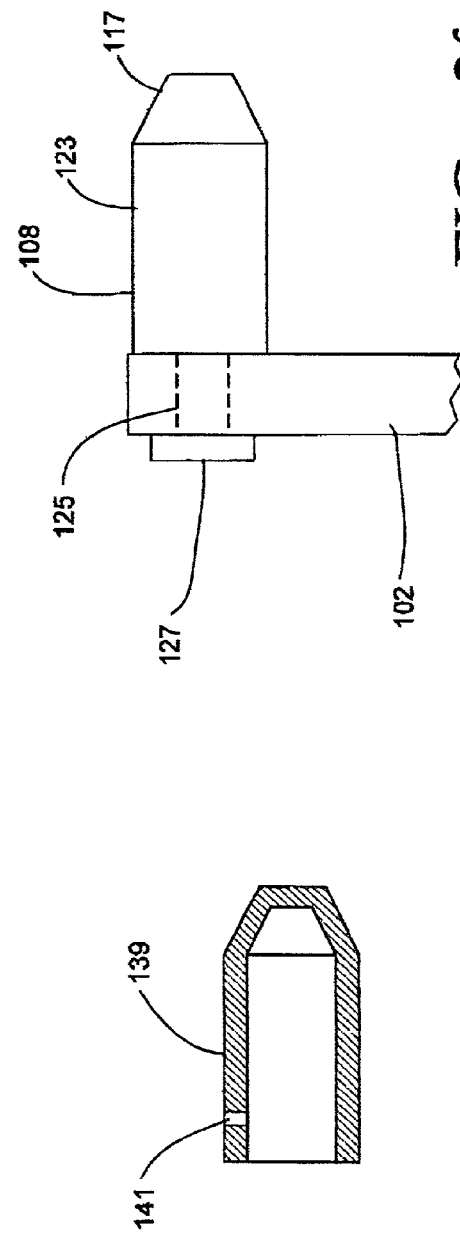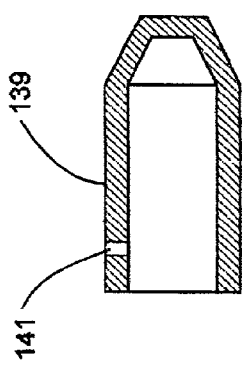

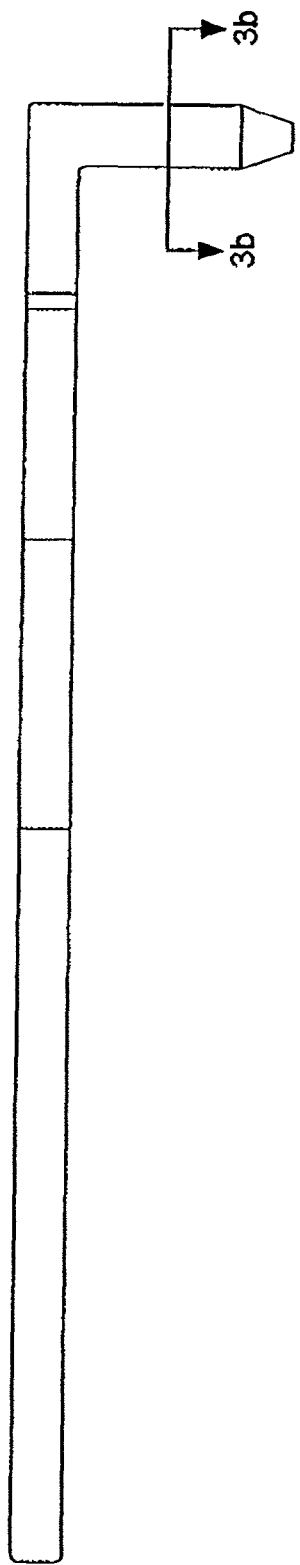
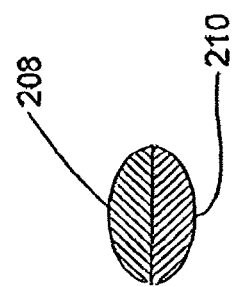
FIG. - 3a
FIG. - 3b

INTERSPINOUS PROCESS IMPLANT SIZER AND DISTRACTOR WITH A SPLIT HEAD AND SIZE INDICATOR AND METHOD

RELATED CASES

This application claims priority to United States Provisional Patent Application entitled INTERSPINOUS PROCESS IMPLANT SIZER AND DISTRACTOR WITH A SPLIT HEAD AND SIZE INDICATOR AND METHOD, filed Sep. 18, 2001, Ser. No. 60/323,508 and is a continuation-in-part of U.S. patent application Ser. No. 09/799,470 filed on Mar. 5, 2001 and entitled SPINAL IMPLANTS, INSERTION INSTRUMENTS, AND METHOD OF USE, now U.S. Pat. No. 6,902,566 issued Jun. 7, 2005, which is a continuation-in-part of U.S. patent application Ser. No. 09/799,215 filed Mar. 5, 2001 now U.S. Pat. No. 7,101,375, which is a continuation-in-part of U.S. patent application Ser. No. 09/473,173 filed on Dec. 28, 1999 and entitled SPINE DISTRACTION IMPLANT, now U.S. Pat. No. 6,235,030 issued May 22, 2001, which is a continuation of U.S. patent application Ser. No. 09/179,570 filed on Oct. 27, 1998 and entitled SPINE DISTRACTION IMPLANT, now U.S. Pat. No. 6,048,342 issued Apr. 11, 2000, which is a continuation-in-part of U.S. patent application Ser. No. 09/474,03 7 filed on Dec. 28, 1999 and entitled SPINE DISTRACTION IMPLANT, now U.S. Pat. No. 6,190,387, issued Feb. 20, 2001, which is a continuation-in-part of U.S. patent application Ser. No. 09/175,645 filed on Oct. 20, 1998 and entitled SPINE DISTRACTION IMPLANT, now U.S. Pat. No. 6,068,630 issued May 30, 2000. All of the above applications and patents are incorporated herein by reference.

FIELD OF THE INVENTION

The present invention relates generally to an apparatus for aiding in the distracting, sizing and/or inserting of an implant into a patient.

BACKGROUND OF THE INVENTION

As the present society ages, it is anticipated that there will be an increase in adverse spinal conditions which are characteristic of older people. By way of example only, with aging comes increases in spinal stenosis (including, but not limited to, central canal and lateral stenosis), the thickening of the bones which make up the spinal column and facet arthropathy. Spinal stenosis is characterized by a reduction in the available space for the passage of blood vessels and nerves. Pain associated with such stenosis can be relieved by medication and/or surgery. Additionally, pain associated with the spines of people of all ages can be caused by other ailments. Of course, in relieving spine related pain no matter what the cause, it is desirable to eliminate the need for major surgery for all individuals and in particular for the elderly.

Thus, there needs to be developed procedures, procedure instrumentations, and implants for alleviating pain associated with the spine, which procedures and implants are minimally invasive, can be tolerated by all patients and particularly by the elderly, and can be performed preferably on an outpatient basis.

SUMMARY OF THE INVENTION

Accordingly, embodiments of the present invention include instrumentation which can provide for easy and convenient distraction and sizing of a surgical site.

The embodiment of the present invention includes a distracting tool comprising first and second distracting prongs, a handle which is operatively connected to the first and second distracting prongs, and wherein when the first and second distracting prongs are placed together, they are about the shape of an implant.

It is a further aspect of the present invention that the distracting tool includes a gauge mechanism for determining the amount of distraction caused by the tool.

In still a further aspect of the present invention, a mechanism is provided that prevents over-distraction of a surgical site.

Yet other aspects of the present invention include distracting prongs which are pivotal, and/or replaceable with prongs of different sizes and/or useable with sleeves in order to increase the size of the distraction prongs.

Further methods of the invention include the use of the above tool in order to distract an implantation site.

Accordingly, it is an object of the present invention to provide a device that can distract an opening.

It is yet another object of the present invention to be able to determine the diameter of the opening without having to remove the distracting device from the opening. A present embodiment of the invention has a gauge which indicates the distance between the distracting prongs, corresponding to the diameter of the opening.

It is yet another object of the present invention to have distracting prongs that are shaped similar to the outer surface of the implant.

It is another object of the present invention to be able to distract the opening and subsequently lock the distracting prongs in place using one hand. Thus, an embodiment of the distracting device of the invention has a locking mechanism that can be controlled with one finger or a thumb.

BRIEF DESCRIPTION OF THE DRAWINGS

FIG. 2*a* is a side view of a portion of the embodiment of the invention of FIG. 2;

FIG. 2*b* is a cross-sectional view of the embodiment of the invention of FIG. 2*a* taken through line 2*b*—2*b*.

FIG. 2*c* is a side view of an embodiment of the invention having interchangeable prongs of different sizes.

FIG. 2*d* is a side view of an embodiment of the invention having interchangeable sleeves of different sizes that fit over the prongs.

FIG. 2*e* is a cross-sectional view of a sleeve of the embodiment of the invention of FIG. 2*d*.

FIG. 2*f* is a side view of yet another embodiment of the invention with the prongs being pivotable.

FIG. 3*a* is a side view of the embodiment of the invention of FIG. 3.

FIG. 3*b* is a cross-sectional view of the embodiment of the invention of FIG. 3*a* taken through line 3*b*—3*b*.

DETAILED DESCRIPTION OF THE INVENTION

Figure 1:
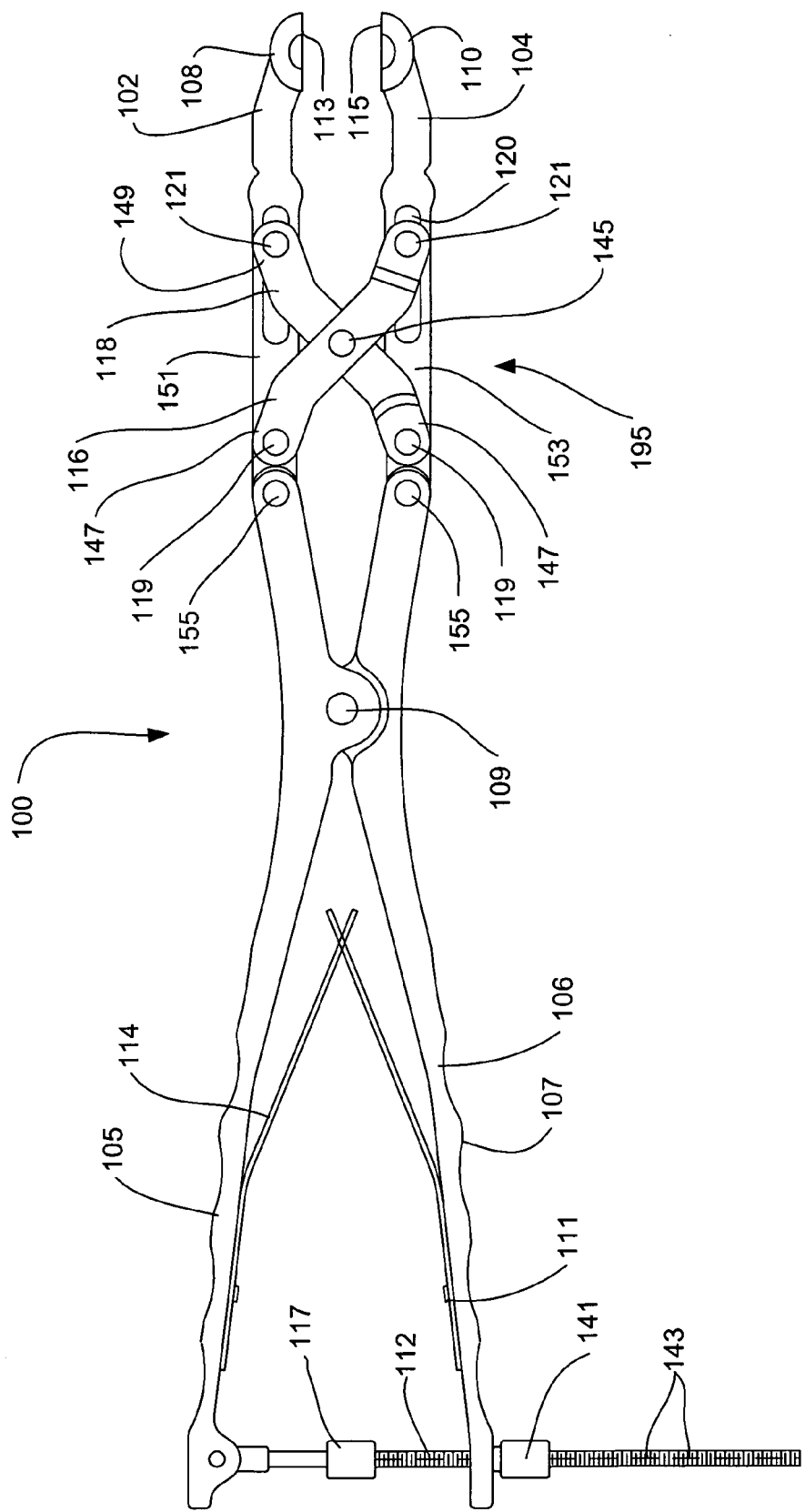
FIG. 1 is a plain view of an embodiment of the present invention illustrating the distracting prongs in an open position.
Figure 2:
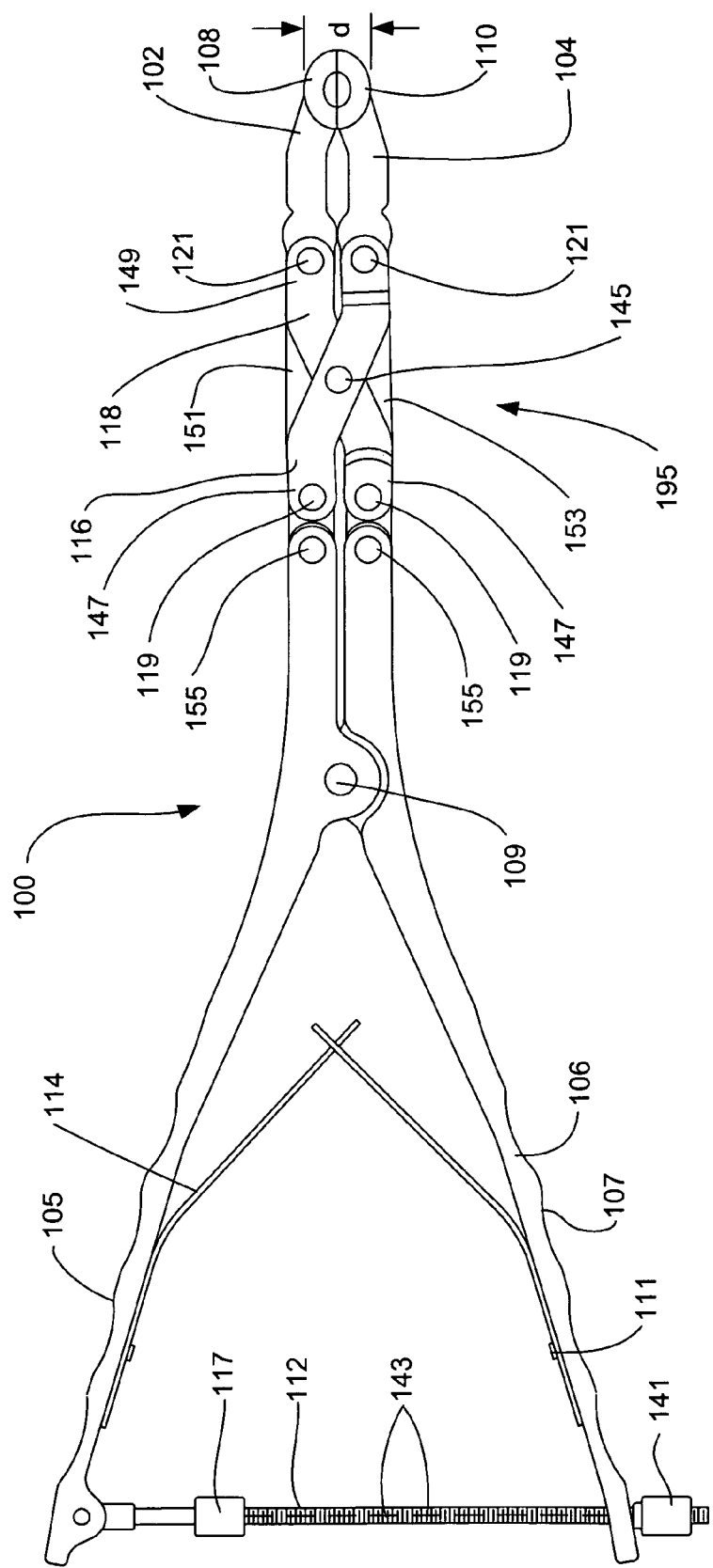
FIG. 2 is a plain view of an embodiment of the present invention illustrating the distracting prong in a closed position.

Embodiment of FIGS. 1 and 2:

Referr to FIG. 1,2 the tool 100,104 is a open,distraction adjacent spinous processed is depicted. The tool 100 has a first distraction prong 102 and a second distraction prong 104. The first distraction prong 102 and the second distraction prong 104 can be seperated to distract an initial opening between adjacent spinous processes. The first distracting prong 102 has a first tip 108 and the second distracting prong 104 has a second tip 110.

FIG. 1 depicts the prongs 102, 104 in an open, distracting position. FIG. 2 shows the prongs 102, 104 closed, with inner surfaces of the prongs 102, 104 touching each other. The inner surfaces 113, 115 are flat in this embodiment. In other embodiments the surface 113, 115 (FIG. 2b) can be concave and of a shape to accept an implant 190 so that the implant 190 can be inserted between the spinous processes with the tool 100 and the prongs 102, 104 still in place between and distracting spinous processes. After the implant 190 is positioned the tool 100 is removed.

As is evident in FIGS. 1, 2 and 2a the prongs 102, 104 when placed together form the shape of an implant 190. The shape in this embodiment has a lead-in nose, or guide or tissue expander 117 (FIG. 2a). This tissue expander 117 includes a cone shape corresponding to the tissue expander 197 of the implant 190, which has in a preferred embodiment an increasing elliptical cross section from a distal end to a place where the tissue expander 117 meets the main body 123. The main body 123 is also preferably elliptical in shape. It is to be understood that other shapes can be used for the prongs including oval, oblong, circular, curved, diamond, and other cylindrical shapes, and be within the spirit and size of the invention. Similar to all the elements of the tool 100, the first distracting prong 102 and the second distracting prong 104 are manufactured from a biologically acceptable material, such as titanium or stainless steel.

In another embodiment of the present invention (FIG. 2f), the first tip 108 and the second tip 110 are separate pivotable or swivelable components attached to the first distracting prong 102 and second distracting prong 104. As seen in FIG. 2f, the main body 123 is pivotably secured to the rest of the prong by a pin 125 extending through a; bore of the prong 102, with a stop 127 keeping the pin in place. As the first tip 108 and the second tip 110 swivel, the physician has additional degrees of freedom to manipulate the handle 106 of the tool as he urges the prongs 102, 104 between adjacent spinous process.

In yet another embodiment (FIG. 2c) of the present invention, the first tip 108 and the second tip 110 are interchangeable. For example, the first tip 108 and the second tip 110 can be replaced with a new first tip 108 and new second tip 110 of a different size, defining a larger or smaller diameter or with a different shape. By way of example only, the tips 108, 110 can be interchangeable with other pairs of tips that when mated together form the approximate shape of one of an implant which is a 6 millimeters, 8 millimeters, 10 millimeters, 12 millimeters, or 14 millimeters implant. The distance in millimeters is that of the spacing or height between adjacent spinous processes. It is to be understood that in the preferred embodiment as shown in FIG. 2, that the prongs and in particular the permanent tips are shaped to approximate a 10 millimeter implant. The 10 millimeter height as seen in FIG. 2 is represented by distance "d."

As can be seen in FIG. 2c, in one embodiment, the interchangeable tips 108, 110 can include a stem 129 which fits through a bore 131 of the prong 102. A ball type detent 133 can be used to secure the tip 108 by having the ball 133 of the detent be received in a groove 135 located on the stem 129 of the removable tip 108. It is to be understood that in this embodiment, as can be seen in FIGS. 1 and 2, that the tip 108 has a cross-section of half of an elliptical shape and thus the stem 129 can have the same shape or can have another shape and fall within the scope of the invention.

In still a further embodiment of the invention as shown in FIGS. 2d and 2e, the tip 108 can itself include a ball type detent 137. In this embodiment, the tip 108 is preferably smaller than the smallest of the preferred sizes, which would be 6 millimeters. That being the case, sleeves 139 can be provided which fit over the end 108 in order to increase the diameter of the end 108. This can be seen in FIG. 2e, the sleeve 139 has an internal shape which can accept the end 108 and a bore 141 which will accept the ball of the detent 137 in order to secure the sleeve 139 in position over the end 108. Sleeves of varying sizes can be provided in order to accommodate individuals with different anatomical shapes. By way of example only, sleeves which can be used in conjunction with implants having heights of 6 millimeters, 8 millimeters, 10 millimeters, 12 millimeters and 14 millimeters. It is also to be understood that the sleeve 139 would have a cross-section as shown in FIGS. 1 and 2, that being half of an elliptical shape in this particular embodiment. As demonstrated above, the sleeves can have other shapes.

As can be seen in all of the embodiments of FIGS. 1 and 2, the tips 108, 110 are provided at about 90° to the rest of the body of the tool 100. It is to be understood that these tips can be provided at other angles both acute and obtuse in order to assist the physician in placing the tips between adjacent spinous processes, in order to distract apart the spinous processes.

With respect to the rest of the tool 100, the handle 106 includes a first member 105 and a second member 107, pivotally connected by a fastener 109. The handle is connected by a linkage 195 to the first and second prongs 102, 104. With respect to handle 106 and for mechanical advantage purposes, the distance from pivot fastener 109 to the below discussed gauge 112 is greater than the distance between pivot fastener 109 and the below discussed fastener 119. The first member 105 and second member 107 each have scallops 111 for use by a physician in order to grip the handle 106.

In this embodiment, a leaf spring 114 is connected between the first member 105 and the second member 107 of the handle 106. The leaf spring 114 biases the handle 106 into an open position, keeping the first prong 102 and the second prong 104 normally closed. The leaf spring 114 also provides resistance to closing the handle 106. One will appreciate that other mechanical devices, such as a coil spring, by way of example, can be used to bias the handle 106 to an open position and provide resistance in closing the handle 106. To spread the first distracting prong 102 and the second distracting prong 104 apart, an individual must urge the first member 105 and the second member 107 of the handle 106 together.

The tool 100 also has a gauge 112. The gauge 112 indicates the distance between the first distracting prong 102 and the second distracting prong 104, which corresponds to the diameter of the opening created between the adjacent spinous processes. The gauge 112 is connected at one end to the first member 105 and passes through the second member 107, extending beyond the second member 107. By way of example only, the gauge 112 can be a threaded screw which is attached to the first member 105 and passes through the second member 107.

A fastener 141 engages the threaded screw adjacent to the second member 107 and limits the movement of the first and second members 105, 107. Further a stop 117 limits the amount of distraction possible with prongs 102, 104. The position of the fastener 141 on the gauge 112 allows a physician to measure the amount by which the handle 106, and thus the amount by which the first prong 102 and the second prong 104 are spread apart in order to distract the space between spinous processes. While distracting the opening, the numbers or markings 143 on gauge 112 that are intercepted by the second member 107 corresponds to the diameter of the opening. Preferably the markings 143 are set to indicate prong openings of 6 mm, 8 mm, 10 mm, 12 mm and 14 mm. The gauge 112 can also increment the first distracting prong 102 and the second distracting prong 104 a known distance apart by rotating the fastener 141 in given amounts.

As previously mentioned, the first distracting prong 102 and the second distracting prong 104 spread apart when the handle 106 is closed. The tool 100 has a linkage 115 that interconnects prongs 102, 114 with the handle. This linkage ensures, in this preferred embodiment, that the first distracting prong 102 and the second distracting prong 104 spread apart in a substantially parallel fashion. As discussed below, other embodiments (FIG. 3) operate in a manner that the prongs are not opened and maintained in a parallel orientation.

The linkage 195 contains a first cross-link 116 and a second cross-link 118. The first cross-link 116 and the second cross-link 118 are pivotally mounted to each other at pivot 145. The first cross-link 116 and the second cross-link 118 have a first end 147 and a second end 149. The first end 147 of both the first cross-link 116 and the second cross-link 118 are pivotally connected with the handle 106 by pivot fasteners 119. The second end 121 of both the first cross-link 116 and the second cross-link 118 slidably engage a slot 120 located in links 151 and 153 of linkage 115. Links 151 and 153 are pivotally pined to first and second members 105, 107 of handle 106 by pivot fasteners 155 at one end, and the prongs 102, 104 extend from links 151, 153 at the other end thereof. Accordingly, with this linkage arrangement 115, the first distracting prong 102 and second distracting prong 104 are limited to substantially parallel motion with respect to each other.

The method of operation of the embodiment of the invention FIGS. 1 and 2 as used by the physician is as follows. After the surgical site between adjacent spinous processes is located, the surgeon can insert the prong distraction ends between the spinous processes using the tissue expansion portion of the ends in order to guide the distracting ends between the spinous processes. After this has occurred, a surgeon can squeeze on the handle 106 in order to urge the prongs apart, thereby distracting the space between the spinous processes. Using the gauge, the surgeon can determine the amount of the distraction, and if required, lock in the distraction by turning the knob which is part of the gauge. Generally in this embodiment, the handle would be moved to a closed position with one hand while the physician can use the other hand to adjust the gauge. It is also to be understood that, if required, the surgeon could urge the handle to a closed position by turning the knob with the gauge. This would give a more exact, incremental way of adjusting the distraction between the spinous processes. By reading the gauge, the physician can determine which size of implant is appropriate for the space. Further if desired, and using tip 108, 110 of FIG. 2b, the physician could then further distract the space in order to create a opening large enough between the distraction prongs in order to slip in an implant between the prongs in the over-distracted position. Once this has been accomplished, the tool 100 can be removed from between the spinous processes with the implant left in place. This procedure would only be used in a situation where it would be acceptable to over-distract the spinous processes. If that is not desirable, then the technique of using the tool 100 to guide the implant in place would not be used.

Figure 3:
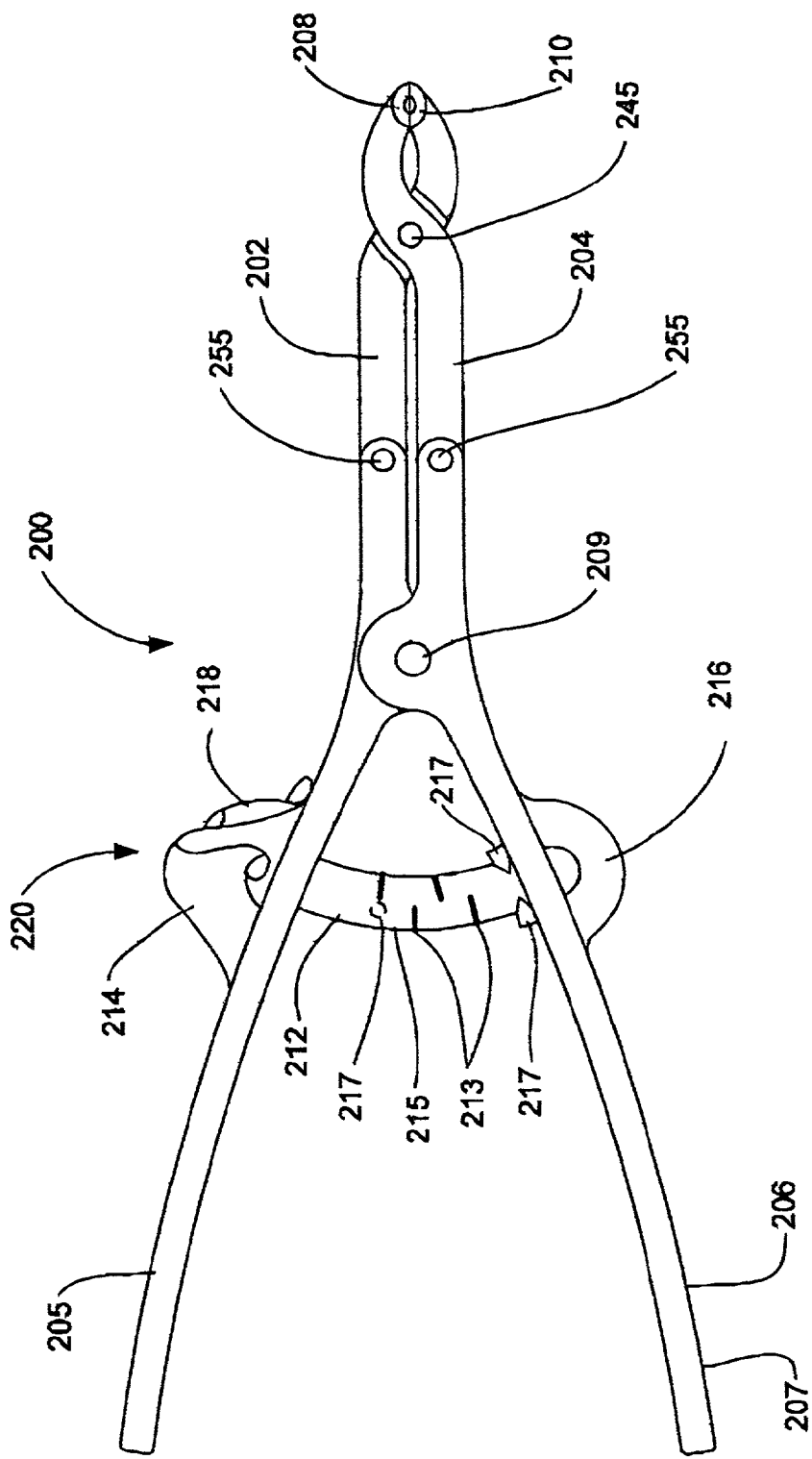
FIG. 3 is a plain view of yet another embodiment of the present invention.
Figure 4A:
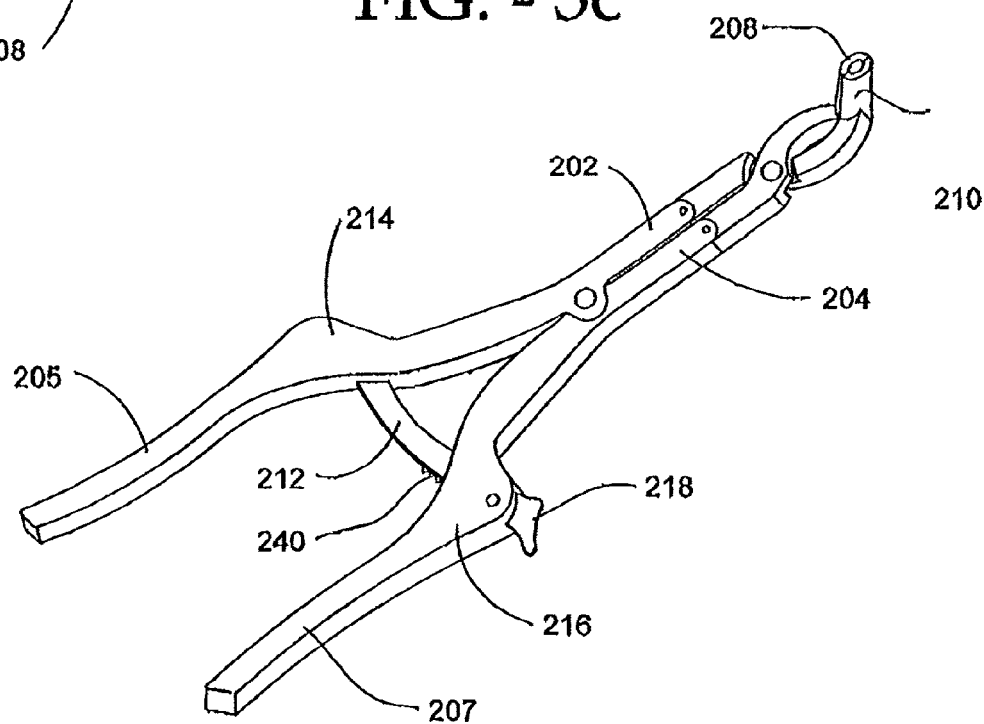
FIG. 4a is a perspective view of an embodiment of the invention similar to FIG. 4 with a locking mechanism.
Figure 4:
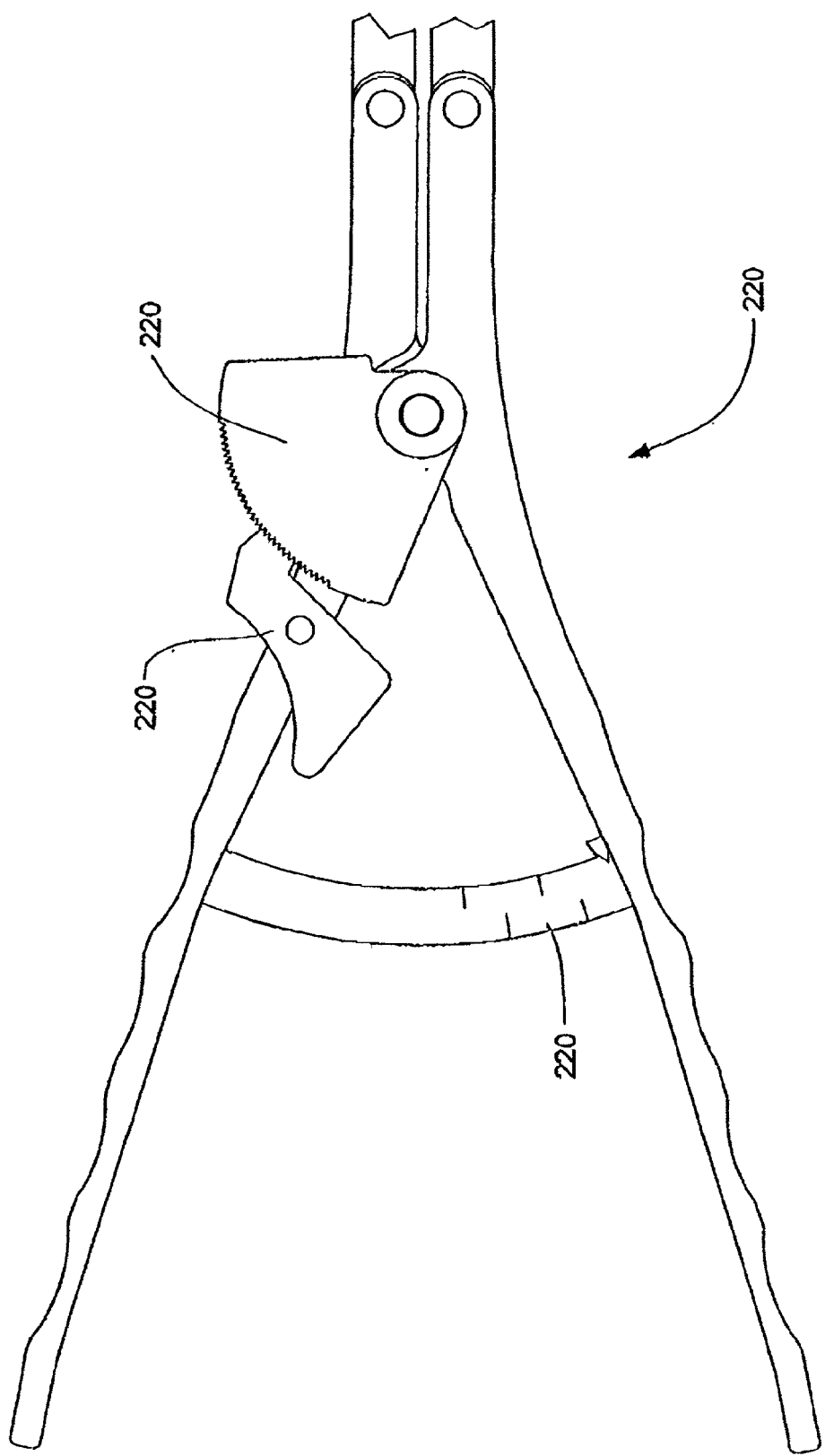
FIG. 4 is a plain view of a locking mechanism of an embodiment of the present invention.

Embodiment of FIGS. 3 and 4:

Referring now to FIGS. 3 and 4, the present invention includes yet another embodiment. The distracting tool 200 has a first distracting prong 202 and a second distracting prong 204. Prongs 202, 204 are pivotally connected at pivot point 245. The first distracting prong 202 has a first distracting end or element 208. The second distracting prong 204 has a second distracting end or element 210. Both the first distracting element 208 and the second distracting element 210 extend out at a substantially 90° angle from the first and second distracting prongs 202,204 in a preferred embodiment FIGS. 3a, 3c) When the first distracting element 208 and second distracting element 210 are closed together, the first distracting element 208 and the second distracting element 210 form the approximate shape of an implant to be inserted into the patient.

The first distracting end or element 208 and the second distracting end or element 210 can have all the features and functionality as previously discussed with respect to prongs 102, 104 and the ends or elements 108, 110 of FIGS. 1 and 2. By way of example only, the first distracting element 208 and the second distracting element 210 can swivel and/or be detachable.

The distracting tool 200 also has a handle 206. The handle 206 is pivotally connected with the first prong 202 and the second prong 204 at pivot points 255. Similar to the previously described embodiments, the first distracting element 208 and the second distracting element 210 are separated by urging handle element 205, 207 of the handle 206 together. Handle element 205 and 207 are pivotally connected at pivot point 209. The handle 206 has a first hand stop 214 and a second hand stop 216 so that a physician may comfortably and positively place his hand around the handle 206.

The distracting tool 200 also has a gauge 212. The gauge 212 is connected with the handle 206 so as to indicate the distance between the first distraction element 208 and the second distraction element 210. By way of example only, the gauge can indicate whether the size of the opening between the adjacent spinous processes is 6 millimeters, 8 millimeters, 10 millimeters, 12 millimeters, or 14 millimeters and/or can accommodate an implant of height 6 millimeters, 8 millimeters, 10 millimeters, 12 millimeters, or 14 millimeters. Indicia 213 are set to these measurements. In this embodiment, gauge 212 has a curved base 215 including the indicia 213, with the base 215 affixed to handle element 205. Base 215 moves relative to handle element 207. Flags or pointers 215 are fixed to handle element 207 and indicate a measurement as base 215 moves thereby.

On the underside, the gauge 212 has a distracting limiter or stop 217 to prevent the handle 206 from being closed beyond a specific limit. The stop 217 is placed on the underside of base 215 and as the handle 206 is urged to a closed position, the stop 217 contracts handle element 207 and prevents further closure of the handle 206 and thus further spreading apart of elements 208, 210. Thus distraction of the spinous processes is limited. For example, the largest implant typically required to be inserted between adjacent spinous processes is 14 millimeters. Accordingly, the distracting limiter 217 is located below the 14 millimeters mark on the underside of the gauge 212. The distracting limiter 217 thus prevents the first distraction element 208 and the second distraction element 210 from spreading apart and creating an opening between the spinous process with a diameter greater than 14 millimeters.

The embodiment of FIG. 3 can be operated in a fashion somewhat similar to that of the embodiment of FIGS. 1 and 2. In this embodiment, however, the distracting elements 208, 210 are not maintained in a parallel orientation. As these elements are opened to heights of upwards of 14 millimeters and it has been found that appropriate distraction can be obtained with the distracting elements 208, 210 not totally maintained in a parallel orientation. With this embodiment, once the tool is inserted between adjacent spinous processes and the handle is urged to a closed position, the amount of distraction of the spinous processes is determined by gauge 212. Once the appropriate distraction is reached, the tool 200 can be locked, holding the distraction at the desired height. The physician can then know the desired height of implant to be selected for implantation. The implant can then be selected from a tray of implants. The tool 200 can then be removed and the process of inserting the implant precedes as disclosed in one the above U.S. patents.

The first hand grip 214 contains a locking mechanism 220 such as the embodiment seen in FIG. 3 or the embodiment seen in FIG. 4. The locking mechanism 220 of FIG. 4 includes a spring-biased and pivotable pawl 222 and a ratchet wheel 224. The pawl 222 has several teeth which engage and interlock with the corresponding teeth of the ratchet wheel 224 when pawl is moved. The pawl (not shown) in FIG. 3 can engage and disengage the ratchet wheel (not shown) by sliding the trigger 218 between a locked and unlocked position. The trigger 218 is placed on the handle 206 such that the trigger 218 can be slidably controlled with a single finger or the thumb. Thus, the physican can maintain the same grip on the handle 206 with only one hand throughout the entire process. For example, the physician can insert the first distracting element 208 and the second distracting element 210 between adjacent spinous process in order to create a first distraction. The handle 206 can then be closed to further distract the initial opening. Upon distracting the opening to the desired diameter, the physician can lock the handle 206 in place by sliding or pushing the trigger 218 into the locked position. FIG. 4a depicts a slightly different embodiment of the invention than that depicted in FIG. 3. However, similar elements have similar numbers. In this case the ratchet wheel is embodied in teeth 240 located on the upper or lower edge of the gauge 212 and the pawl is incorporated in the pivotable trigger 218.

Figure 3C:
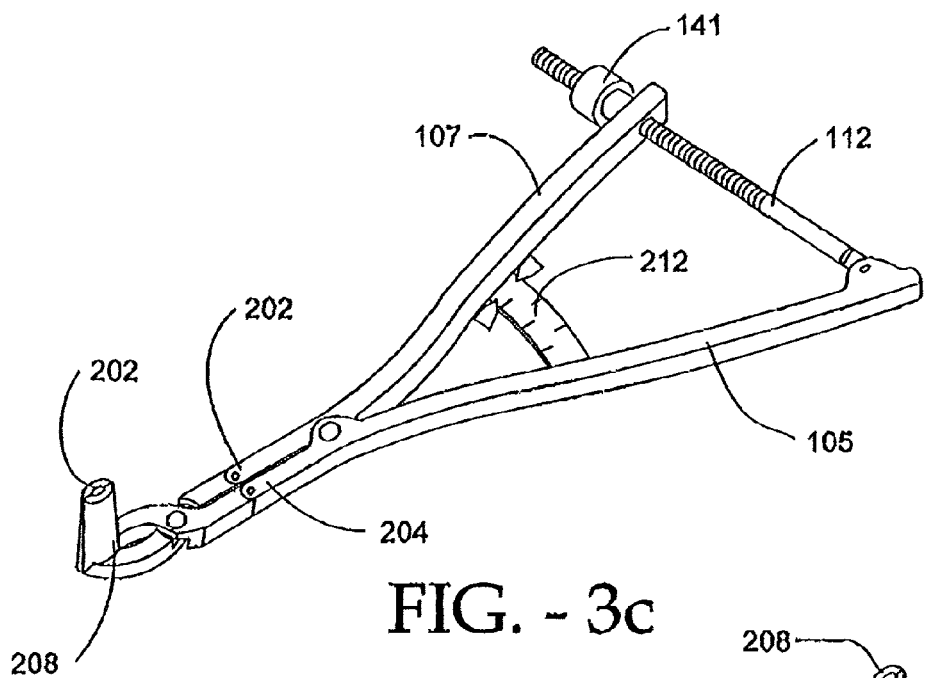
FIG. 3*c* is a perspective view of an embodiment of the invention which has some of the features depicted in FIG. 3.

Alternatively FIG. 3c depicts an embodiment of the invention with a gauge 212 as depicted in FIG. 3 and a locking mechanism 112, which can be designed to also include a gauge, as depicted in FIG. 1. Similar elements have similar numbers.

The present invention includes a method of sizing, and distracting an opening, and subsequently and alternatively installing an implant device between adjacent spinous processes. Preferably, a physician will first create an initial opening in the body tissue between the adjacent spinous processes. Referring now to the embodiment as illustrated in FIGS. 1, 2, a physician can then insert the ends or distracting elements the first distracting prong 102 and the second distracting prong 104 into the initial opening. By pressing the handle 106 together, the first distracting prong 102 and the second distracting prong 104 will spread apart, further distracting the initial opening. The physician can continuously read the gauge 112 to determine the distance between the first distracting prong 102 and the second distracting prong 104. The physician does not have to remove the tool 100 to measure the diameter of the opening.

When the physician distracts the opening to the desired diameter, the tool 100 can be locked in place. The physician can then select an implant with a similar diameter. The physician can then remove the tool 100 and insert the implant as described in cases of the above referenced patents. Alternatively, if appropriate, while the first distracting prong 102 and the second distracting prong 104 are still within the opening, the physician can then urge the implant between the first distracting tip 108 and the second distracting tip 110. As mentioned previously the first tip 108 and the second tip 110 form a channel to guide the implant. To leave the implant within the patient, the physician can remove the tool 100 from between the adjacent spinous processes.

Referring now to the embodiment illustrated in FIGS. 3 and 4, the same method can be followed as previously described above. A physician can insert the first distraction element 208 and the second distraction element 210 into the opening. By closing the handle 206 together, the first distraction element 208 and the second distraction element 210 will spread apart. The gauge 212 indicates the diameter of the opening.

When the desired diameter is reached, the handle 206 can be locked into place. By sliding the trigger 218 into the "locked" position, the first destruction element 208 and the second distraction element 210 are locked in place. Selecting an appropriately sized implant, inserting the implant and removing the tool 200 are all similar to the previously described embodiment.

The foregoing description of preferred embodiments of the present invention has been provided for the purposes of illustration and description. It is not intended to be exhaustive or to limit the invention to the precise forms disclosed. Many modifications and variations will be apparent to practitioners skilled in the art. The embodiments were chosen and described in order to best explain the principles of the invention and its practical application, thereby enabling others skilled in the art to understand the invention with various embodiments and with various modifications as are suited to the particular use contemplated. It is intended that the scope of the invention be defined by the following claims and their equivalents.

The invention claimed is:

1. A method for determining the size of an opening for installing an implant, the method comprising:
   (a) inserting distracting prongs between body elements wherein at least a portion of the first and second distracting prongs is a tissue expander having a varying width that increases from a first width to a second width;
   (b) distracting the body elements by increasing the distance between distracting prongs such that the distracting prongs remain substantially parallel;
   (c) reading a gauge to determine the distance between the distracting prongs;

(d) removing the distracting prongs from between the elements such that the body elements remain at least partially distracted;

(e) selecting the implant based on reading the gauge; and (f) positioning the implant between the body elements.

2. A system for distracting adjacent spinous processes, said system comprising:

a implant; and a distraction tool including:

a first distracting prong and a second distracting prong;

a handle operatively connected to the first and the second distracting prongs;

said handle operable to spread the first and second distracting prongs apart such that the first and second distracting prongs are spread apart in a substantially parallel fashion; and first and second sleeves adapted to fit over the first and second distracting prongs in order to increase the size of the first and second distracting prongs.

3. A system for distracting adjacent spinous processes, said system comprising:

an implant; and a distraction tool including:

a first distracting prong and a second distracting prong wherein at least a portion of the first and second distracting prongs is a second tissue expander have a varying width that increases from the second width to the first width;

means for controlling the separation between the first and second distracting prongs such that the first and second distracting prongs are spread apart in a substantially parallel fashion;

means for determining the distance between the first and second distracting prongs;

means for locking the first and second distracting prongs in place;

wherein the means for controlling the separation between the first and second distracting prongs and the means for locking the first and second distracting prongs in place can be operated with one hand; and first and second sleeves adapted to fit over the first and second distracting prongs in order to increase the size of the first and second distracting prongs.

4. A method of arranging an implant between adjacent spinous processes, the method comprising:

inserting distracting prongs between spinous processes wherein at least a portion of the first and second distracting prongs is a first tissue expander have a varying width that increases from a first width to a second width;

distracting the spinous processes by increasing the distance between distracting prongs;

reading a gauge to determine the distance between the distracting prongs;

removing the distracting prongs from between the spinous processes such that the spinous processes remain at least partially distracted;

selecting the implant based on reading the gauge, the implant including a spacer having the second width and a second tissue expander having a varying width that increases from the first width to the second width; and positioning the implant between the spinous processes.

\* \* \* \* \*